(12) United States Patent
Breuer-Ruesch et al.

(10) Patent No.: US 11,872,145 B2
(45) Date of Patent: Jan. 16, 2024

(54) LINEAR FORCE-MEASURING DEVICE AND HYDRAULIC ACTUATOR

(71) Applicant: Otto Bock Healthcare Products GmbH, Vienna (AT)

(72) Inventors: Christian Breuer-Ruesch, Vienna (AT); Andreas Gradischar, Vienna (AT); Juan Pablo Mejia Nino, Vienna (AT); Roland Auberger, Vienna (AT); Alexander Noah Spring, Ottawa (CA)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 336 days.

(21) Appl. No.: 15/733,177

(22) PCT Filed: Dec. 11, 2018

(86) PCT No.: PCT/EP2018/084324
§ 371 (c)(1),
(2) Date: Jun. 4, 2020

(87) PCT Pub. No.: WO2019/115513
PCT Pub. Date: Jun. 20, 2019

(65) Prior Publication Data
US 2020/0383805 A1    Dec. 10, 2020

(30) Foreign Application Priority Data
Dec. 11, 2017 (DE) ............... 10 2017 129 486.4

(51) Int. Cl.
*G01L 5/00* (2006.01)
*A61F 2/76* (2006.01)
(Continued)

(52) U.S. Cl.
CPC ............. *A61F 2/76* (2013.01); *A61F 2/68* (2013.01); *F16C 35/047* (2013.01);
(Continued)

(58) Field of Classification Search
CPC ............................. G01L 5/0009–0023
See application file for complete search history.

(56) References Cited

U.S. PATENT DOCUMENTS 3,824,846 A * 7/1974 Andersson ............ G01L 5/0019
73/862.633
3,992,931 A * 11/1976 Tranquilla ............ G01L 5/0019
73/862.041
(Continued)

FOREIGN PATENT DOCUMENTS

CN    202614432 U    12/2012
DE    69209476 T2    1/1997
(Continued)

OTHER PUBLICATIONS

"International Search Report and Written Opinion of the International Searching Authority," issued in connection with Int'l Appl. No. PCT/EP2018/084324, dated Jul. 15, 2019 (28 pages).
(Continued)

*Primary Examiner* — Alexander A Mercado
(74) *Attorney, Agent, or Firm* — HOLLAND & HART LLP (57) ABSTRACT

A linear force-measuring device for a hydraulic actuator of an orthopedic device. The force-measuring device includes a base, a bearing receptacle and at least one sensor for detecting changes in length between the base and the bearing receptacle, wherein the bearing receptacle is connected to the base via two opposing connecting parts, and the at least one sensor is secured to one of the connecting parts.

22 Claims, 8 Drawing Sheets (51) Int. Cl.
*A61F 2/68* (2006.01)
*F16C 35/04* (2006.01)
*A61F 2/74* (2006.01)

(52) U.S. Cl.
CPC .............. *G01L 5/0019* (2013.01); *A61F 2/74* (2021.08); *A61F 2002/7635* (2013.01); *F16C 2316/10* (2013.01)

(56) References Cited

U.S. PATENT DOCUMENTS

| | | | | |
|---|---|---|---|---|
| 4,326,424 | A * | 4/1982 | Koenig | G01L 5/0019 73/862.633 |
| 4,735,102 | A * | 4/1988 | Koenig | G01L 5/107 73/862.634 |
| 4,796,474 | A * | 1/1989 | Koenig | F16C 13/02 73/862.633 |
| 4,899,599 | A * | 2/1990 | Eddens | G01L 1/2243 73/862.633 |
| 4,958,525 | A * | 9/1990 | Hauer | G01L 5/1627 73/862.633 |
| 5,113,709 | A * | 5/1992 | Ekola | G01L 5/108 73/862.638 |
| 5,250,762 | A * | 10/1993 | Gustafsson | G01L 5/106 177/244 |
| 5,777,240 | A * | 7/1998 | Lefebvre | G01L 5/0019 177/229 |
| 6,161,962 | A * | 12/2000 | French | G01L 5/0023 384/459 |
| 2008/0226409 | A1 * | 9/2008 | Hasenzahl | G01L 1/2231 409/188 |
| 2008/0307898 | A1 * | 12/2008 | Haaser | G01L 5/101 73/862.06 |
| 2009/0208158 | A1 | 8/2009 | Guillaume et al. | |
| 2021/0040987 | A1 * | 2/2021 | Riedel | G01L 5/0004 |
| 2022/0003268 | A1 * | 1/2022 | Pizzi | F16C 19/522 |

FOREIGN PATENT DOCUMENTS

| | | |
|---|---|---|
| DE | 19917020 A1 | 11/2000 |
| DE | 10139333 A1 | 3/2003 |
| EP | 1528382 A1 | 5/2005 |
| EP | 1696216 A1 | 8/2006 |
| EP | 2090793 A1 | 8/2009 |
| WO | 1994007118 A1 | 3/1994 |
| WO | 2002002450 A1 | 1/2002 |
| WO | 2011123928 A1 | 10/2011 |

OTHER PUBLICATIONS

"Invitation to pay additional fee of the International Searching Authority," issued in connection with Int'l Appl. No. PCT/EP2018/084324, dated Mar. 14, 2019 (9 pages).

* cited by examiner

LINEAR FORCE-MEASURING DEVICE AND HYDRAULIC ACTUATOR

CROSS REFERENCE TO RELATED APPLICATIONS

This application is a U.S. National Entry and claims priority to PCT International Patent Application No. PCT/EP2018/084324, filed 11 Dec. 2018, and entitled "LINEAR FORCE-MEASURING DEVICE AND HYDRAULIC ACTUATOR", which claims priority to Germany Patent Application No. 10 2017 129 486.4 filed 11 Dec. 2017, the entire disclosures of which are incorporated herein by this reference.

TECHNICAL FIELD

The invention relates to a linear force measurement device for a hydraulic actuator of an orthopedic device, having a base, a bearing receptacle, and at least one sensor for detecting changes in length between the base and the bearing receptacle, and also a hydraulic actuator having such a linear force measurement device.

BACKGROUND

In orthopedic devices such as orthoses and prostheses or on wheelchairs, sensor data require to be made available in order to determine loads or load change cycles or to control hydraulic actuators such as hydraulic dampers and/or hydraulic drives, on the basis of which data, for example, drives are activated or valves adjusted, motion patterns detected or component loads calculated. Loads can be detected via pressure sensors or moment sensors, for example.

A further possibility for measuring forces on the basis of changes in length lies in the arrangement of strain gauges for detecting elongations or compressions. In order to detect forces that act on a linear actuator or that are exerted by a linear actuator, strain gauges are fastened to the linear actuator. A problem in the detection of the forces is that, with the same load, different installation positions can lead to different measurement values. In addition, a modular set-up is not provided, and the signal quality is often not very high.

SUMMARY

The object of the present invention is therefore to make available a linear force measurement device which provides a high signal quality in different uses and installation situations of a hydraulic actuator.

According to the invention, this object is achieved by a linear force measurement device having the features disclosed herein, and by a hydraulic actuator having the features also disclosed herein. Advantageous embodiments and developments of the invention are disclosed in the description and the figures.

In the linear force measurement device for a hydraulic actuator of an orthopedic device, having a base, a bearing receptacle, and at least one sensor for detecting changes in length between the base and the bearing receptacle, provision is made that the bearing receptacle is connected to the base via two mutually opposite webs, and that the at least one sensor is fastened to one of the webs. By virtue of the fact that a bearing receptacle, serving to fasten a hydraulic actuator to a further component of the orthopedic device, for example a prosthesis or orthosis, is connected to a base via which the linear force measurement device can be coupled to the hydraulic actuator, it is possible to obtain a cost-effective, modular set-up of orthopedic components. By way of the webs, sufficient space can be made available for the fastening of a sensor or of several sensors. The arrangement of the sensor on the webs permits optimized fastening and ensures a high signal quality. The connection of the bearing receptacle to the base via two webs creates a symmetrical transmission of force such that, when tensile forces or compressive forces are applied between the bearing receptacle and the base, these forces are forwarded in a uniform manner. Bending moments, which can influence a force measurement, are thereby reduced or excluded. In addition, a high degree of stiffness is achieved by the two webs spaced apart from each other, lying opposite each other, and preferably oriented parallel to each other. The performance capabilities of the strain gauge are thus utilized optimally. The sensor or the sensors are designed in particular as strain gauges or piezo elements.

The webs can be designed as walls, as a result of which a maximum degree of stiffness can be achieved at a low weight, without the signal strength of the sensor being reduced. The webs are preferably of trapezoidal shape and taper in the direction of the bearing receptacle such that, in the case of an isosceles trapezoid, the longer of the two parallel sides is located at the base, while the shorter of the parallel sides is located at the bearing receptacle. The axis of symmetry of the trapezoidal wall is preferably arranged centrally at the bearing receptacle, such that the forces introduced into the linear force measurement device via the bearing receptacle are distributed uniformly to the webs and effect a uniform lengthening or compression.

The webs can have a uniform wall thickness in order to create a homogeneous stress field and to obtain a precise signal via the sensor, e.g. strain gauge or piezo element.

The webs are preferably oriented parallel to the force action direction, i.e. they extend from the base to the bearing receptacle in the force action direction of the linear force acting from the bearing receptacle to the base and back. The webs are preferably oriented parallel to each other in order to avoid, as far as possible, bending moments and transverse forces of the kind that could occur if the webs were arranged obliquely in relation to the force action direction. In principle, it is also possible to permit a slight inclination of the webs relative to the force action direction.

In a development of the invention, provision is made that the base is configured as a round disk, on which the linear force measurement device bears with its full surface area or at least its full circumference on a corresponding receptacle, for example of a hydraulic actuator. It is thereby possible to fasten the linear force measurement device rotatably on the respective object, such that a desired orientation of the linear force measurement device relative to the fastening location can be effected at the bearing receptacle end or the base end. The base can also have at least one shoulder or a circumferential projection, via which the base can be centered or oriented at or in a receptacle of a further component.

The bearing receptacle is preferably sleeve-shaped with a round recess, so as to be able to secure the bearing receptacle to a bearing on corresponding fastening elements such as bolts, pins, a fastening frame or the like. By virtue of the round shape of the recess, it is possible for the conventional bearings, in particular self-aligning bearings such as self-aligning rolling bearings or self-aligning sliding bearings or also ball-joint bearings, to be arranged in the bearing receptacle, such that a possibility of substantially adjusting the linear force measurement device relative to the bearing site can be achieved without transverse forces, twisting or warping occurring inside the linear force measurement device. In addition, by virtue of the rotatability about at least two rotational degrees of freedom, use on the right side or left side is possible in the case of lateral arrangement on orthopedic devices such as in particular orthoses or prostheses, such that there is extensive decoupling of stress in the linear force measurement device. This has the effect that it is only the linear forces that occur between the bearing receptacle and the base toward each other or away from each other that are measured via the sensor or the sensors, e.g. the strain gauge or the strain gauges.

The base, the webs and the bearing receptacle can be formed in one piece, for example sintered or cast or produced in another primary shaping method. The manufacturing outlay is thus reduced, and force is introduced from the base into and through the bearing receptacle in a uniform manner.

In a development of the invention, provision is made that a stiffening element is arranged between the webs. The stiffening element, arranged between the webs, affords a further stiffening of the webs. In this way, when tensile forces or compressive forces are applied, bending effects or a tendency to buckling are eliminated, such that it is possible to obtain a very linear characteristic both in the tension direction and also in the pressure direction.

In a preferred embodiment, the stiffening element is designed as a wall, which runs between the webs. The webs are preferably oriented parallel to each other, such that the wall as stiffening element extends perpendicularly to the respective web. The wall can extend over the entire region between the base and the bearing receptacle, such that it can be connected both to the bearing receptacle and to the base. The webs are moreover connected to the stiffening element such that, particularly if the stiffening element is arranged centrally in the region of the plane arranged along the symmetry of the trapezoidal webs and extending perpendicularly therefrom in the direction of the opposite web, there is a symmetrical configuration of the webs and of the stiffening element. The contour of the stiffening element together with the two webs corresponds to or is similar to an I-beam or an H-beam, as a result of which it is possible to achieve a high degree of stiffness along with a reduced use of material, and therefore a compact structure with a low weight. The stiffening element in the form of a wall effectively prevents bending of the webs, particularly in the event of compression of the webs. The stiffening element is preferably arranged centrally with respect to the bearing receptacle, such that the stiffening element, particularly when configured as a wall, lies in a plane of symmetry for the linear force measurement device.

The base, the webs and the bearing receptacle, in conjunction with the stiffening element, form a receiving space, particularly if the stiffening element bears on the base and also on the webs and the bearing receptacle. The receiving space, which is open at one side, can accommodate control electronics or evaluation electronics which are connected to the sensor, e.g. strain gauge or piezo element, preferably via a cable connection, in particular a flat ribbon cable. In a symmetrical configuration of the stiffening element, particularly when it bears fully on the base, the webs and the bearing receptacle, two receiving spaces are formed to both sides of the stiffening element or of the stiffening wall, such that, on mutually opposite sides of the stiffening element, sufficient space is formed by the webs, the bearing receptacle and the base, for example in order to arrange therein a second control device for a second sensor. Similarly, transmission devices or attachments can be arranged in the receiving space. The sensor or sensors and the evaluation and/or control electronics can be cast in a plastic and encapsulated by the latter, in order to obtain mechanical protection of the electronics. The sensor is preferably secured to the outside of the web or of a web, in order to utilize the preferably flat surface that is available there.

The hydraulic actuator according to the invention, which can be configured for example as a hydraulic damper or a hydraulic drive or a combination thereof and which is equipped for an orthopedic device with a piston-cylinder unit and has a receptacle at which or in which a linear force measurement device as described above is arranged, has the advantage that, with a high degree of stiffness, forces can be introduced from a bearing point of the hydraulic actuator into the hydraulic actuator via the linear force measurement device, for example in order to convey forces from a prosthesis upper part or orthosis upper part to a prosthesis lower part or orthosis lower part or to take up such forces. At the same time, the tensile or compressive forces occurring there can be measured via the sensor and can be used to control the hydraulic actuator. For this purpose, the measured forces are evaluated by the evaluation and/or control electronics and are converted into control signals, via which drives are either activated or deactivated in order to move the piston-cylinder unit relative to each other or to open or close valves. By virtue of the linear force measurement device being fastened at or in a receptacle, it is possible to couple different hydraulic components to the linear force measurement device. It is additionally possible to couple a measurement device at the same time as connecting the hydraulics to the orthopedic component, such that the linear force measurement device at the same time forms the connection between the orthopedic device and the hydraulic component. By arranging the linear force measurement device in the receptacle of the hydraulic actuator, the force can be measured substantially independently of bending moments inside the hydraulic unit. In a development of the invention, provision is made that the base of the linear force measurement device bears with its complete surface area or at least with its complete circumference on the receptacle. Particularly in conjunction with a round shape of the base and a correspondingly round receptacle, it is possible to arrange the linear force measurement device rotatably on the hydraulic actuator. By virtue of the base bearing on the receptacle or in the receptacle with its complete surface area or at least with its complete circumference, it is possible to achieve a uniform introduction of force into the base, independently of the orientation of the linear force measurement device. In this way, the force to be conveyed is transmitted fully from the base to the webs. A deformation or a point-by-point introduction of force is reduced or excluded.

If the base is mounted rotatably at or in the receptacle, the base is advantageously fixed at the receptacle by clamping. This camping can be effected, for example, by a union nut which is screwed onto an external thread at the receptacle and presses the base uniformly in the direction of the receptacle and clamps it thereon.

A self-aligning bearing or a ball joint is preferably arranged in the bearing receptacle, such that the entire hydraulic actuator can be moved in at least two rotational degrees of freedom relative to the orthopedic device. This results in an almost stress-free introduction of force from the fastening devices of the orthopedic device into the hydraulic actuator via the linear force measurement device. The receptacle can therefore be formed or arranged, for example, on a housing of the hydraulic actuator or a piston rod, such that the clamping can be effected via the union nut or via another clamping device at almost any desired location of the hydraulic actuator. The positioning either on the housing or a piston rod is effected according to the geometrical circumstances and the requirements of the orthopedic device.

With the solution according to the invention, it is possible to achieve a position-independent fastening of the sensor, e.g. of the strain gauge or piezo element, as force sensor in relation to the hydraulic actuator, in particular independently in relation to the housing or a piston rod as regards the longitudinal extent or the force action line. By way of the linear force measurement device, a sensor carrier, in particular a strain gauge carrier or piezo element carrier, is made available which additionally defines the connection of a hydraulic actuator to the orthopedic device. The linear force measurement device is arranged so as to be adjustable, in particular rotatable, relative to the hydraulic unit, such that, by use of the modular assemblies, a hydraulic actuator for example can be arranged to the left or right laterally on an orthosis or prosthesis.

The geometry of the linear force measurement device results in a homogeneous stress field along with a small overall volume and very high strength. A linear characteristic in the tension and pressure direction can thus be achieved with a high signal quality.

BRIEF DESCRIPTION OF THE DRAWINGS

An illustrative embodiment of the invention is explained in more detail below with reference to the accompanying figures, in which.

DETAILED DESCRIPTION

Figure 1:
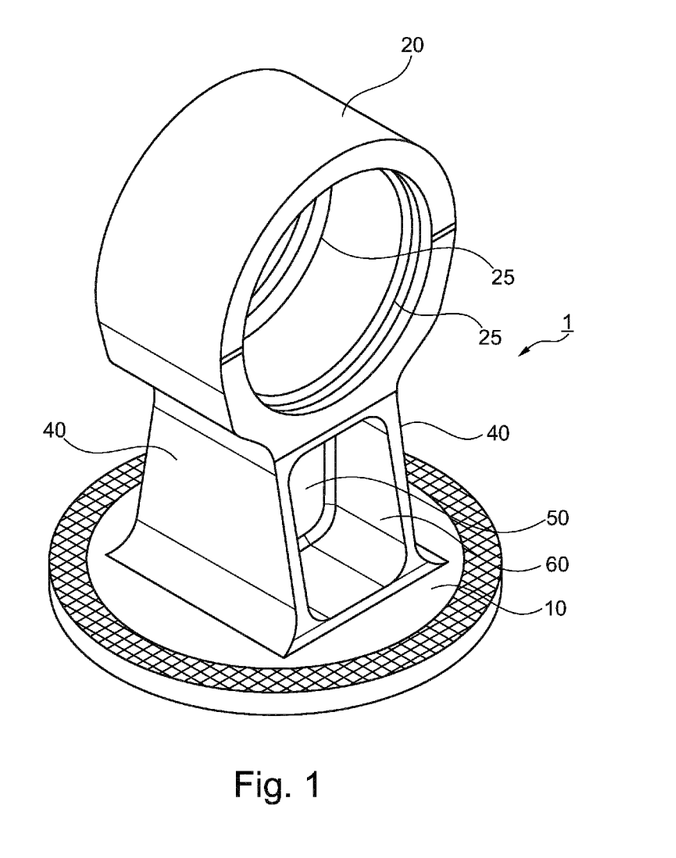
FIG. 1 shows a perspective view of a linear force measurement device without strain gauge.

FIG. 1 is a perspective view showing a linear force measurement device 1 for a hydraulic actuator of an orthopedic device, for example an orthosis, exoskeleton, prosthesis or wheelchair, said linear force measurement device 1 having a base 10 which, in the illustrative embodiment shown, is disk-shaped and round. On a top face of the base 10, a bearing receptacle 20 is connected to the base 10 by two webs 40. In the illustrative embodiment shown, the base 10, the bearing receptacle 20 and the webs 40 are produced in one piece, for example drop-forged, cast, sintered or pressed. In an alternative embodiment of the invention, the base 10 can be formed separately from the bearing receptacle 20 and the webs 40, wherein the bearing receptacle 20 and the webs 40 are either formed in one piece or are produced from separate components and connected to each other. In addition to production by primary forming, the base 10, bearing receptacle 20 and webs 40 can be produced in the context of a separating method and/or reshaping method. If separate parts are produced, there are preferably cohesively bonded to each other, in particular welded. The base 10 and also the webs 40 and the bearing receptacle 20 are preferably produced from a metal, in particular a light metal or another high-strength material. Production using fiber-reinforced plastics is also possible. In one embodiment, the underside of the base 10, directed away from the bearing receptacle 20, has a circumferential shoulder, such that a raised, circular socket is formed on the underside. It is additionally possible that the base 10 bears with its full circumference on an annular support at or in a receptacle of a hydraulic actuator. In addition, the base 10 is centered inside the receptacle via the socket. As an alternative to a shoulder or a circular projection, it is possible for the underside of the base 10 to be designed flat or smooth, such that it can bear with its complete surface area on a correspondingly shaped surface of the receptacle.

The two webs 40 are oriented parallel to each other and, in the direction away from the base 10 to the bearing receptacle 20, they can either likewise extend parallel or can have a slight inclination with respect to each other. In the case of a parallel orientation of the webs 40 with respect to each other, and of a substantially orthogonal orientation of the webs 40 away from the base 10 in the direction of the bearing receptacle 20, tensile forces and compressive forces that are transmitted from the bearing receptacle 20 to the base 10 via the webs 40 are conveyed rectilinearly through the webs 40, thereby providing an almost ideal elongation or compression of the webs 40 at a corresponding load. At least one strain gauge or several strain gauges can then be arranged on the outside of the webs 40 in order, by the measurement of changes in length, to detect tensile forces and compressive forces that are transmitted through the webs 40 into the base 20 via the bearing receptacle 10.

The bearing receptacle 20 is sleeve-shaped and has, on the inner face of its end regions, grooves 25 in which spring rings or other securing disks or securing elements can be inserted in order to secure a bearing body (not shown in FIG. 1), for example a sliding bearing body or rolling bearing body, against axial displacement out of the bearing receptacle 20.

The bearing receptacle 20 sits on the two webs 40 and preferably centrally on the base 10, thus resulting in an axially symmetrical set-up both with respect to a plane perpendicular to the axis through the recess through the bearing receptacle 20 and orthogonal to the base 10, and likewise an axially symmetrical plane orthogonal to the base 10 and parallel to the extent of the webs 40, wherein the notional axis of the recess of the bearing receptacle 20 extends in the second plane of axial symmetry.

Arranged between the webs 40 is a stiffening element 50 which, in the illustrative embodiment shown, is designed as a wall that extends between the inner faces, i.e. the two mutually facing sides, of the webs 40. The wall as stiffening element 50 extends across the full width of the space between the two webs 40 and is connected to the webs 40. The stiffening element 50 can be inserted separately and can be adhesively bonded or welded or soldered to the webs 40, which are designed as walls. Alternatively, the wall 50 can also be formed in one piece with the webs 40 and/or the base 10 and/or the bearing receptacle 20. The wall 50 as stiffening element extends substantially orthogonally to the base 10 and within the plane of axial symmetry and can be connected to the base 10, for example by adhesive bonding, welding, soldering or in some other way. The stiffening element 50 can likewise be connected to the outside or underside of the bearing receptacle 20, in particular by adhesive bonding, soldering, welding or in some other way. An important role of the stiffening element 50 is to prevent the tendency of the webs 40 to buckle when a compressive load is applied and to prevent a tendency to bending when a tensile load is applied, such that an improved signal quality can be achieved by a change in length within the webs when a tensile load or compressive load is applied.

Between the webs 40, a foot region can be formed on the bottom directed toward the base 10, which foot region has a widened configuration, and therefore, at the transition of the webs 40 to the base 10, a widening is obtained, such that forces applied through the webs 40 are introduced uniformly into the base 10. On both sides of the stiffening element 50, a receiving space 60 is delimited by the webs 40, the base 10 or the foot region and the bearing receptacle 20, which receiving space 60 has an opening at one side, such that electrical or electronic components can be inserted into the receiving space 60.

The webs 40 can have a trapezoidal shape, i.e. can taper from the foot region in the region of the base 10 to the head region in the region of the bearing receptacle 20. It is also possible in principle that the webs have parallel front faces, which is in particular useful only when the bearing receptacle 20 is comparatively wide and covers a large part of the surface of the base 10. It is in principle also possible, and part of the invention, that no stiffening element 50 is arranged between the webs.

Figure 2:
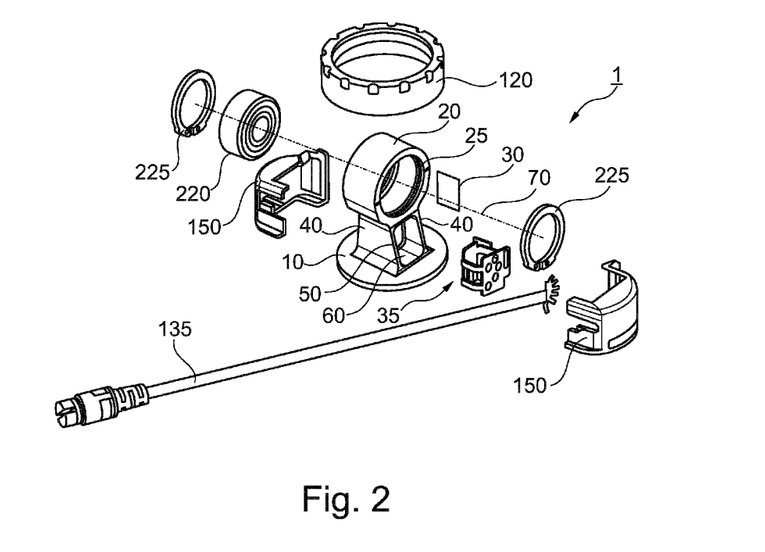
FIG. 2 shows an exploded view of a linear force measurement device.

FIG. 2 is an exploded view showing the linear force measurement device 1 with the base 10, the two webs 40, the bearing receptacle 20, and the stiffening element 50 arranged between the webs 40. In this illustrative embodiment too, the base 10 is designed as a circular disk. A sensor 30 in the form of a strain gauge 30 is shown separated from one outer face of a web 40. In addition to a strain gauge, the sensor 30 can also have another form or another operating principle, e.g. it can be configured as a piezo element. Where a strain gauge 30 is mentioned below by way of an example, this covers all suitable sensors. The strain gauge 30 is fastened to the outer face of the web 40 by suitable measures, for example by bonding, and is coupled to an electronic evaluation and/or control device 35. The electronic evaluation and/or control device 35 is dimensioned such that it can be inserted into the receiving space 60 that is delimited by the base 10, the webs 40, the bearing receptacle 20 and the stiffening element 50. On the outer face of the evaluation and/or control device 35, the measured values of the strain gauge 30 can be recovered for further use via finger-like contact terminals and a cable 135. For the bearing receptacle 20, a bearing body 220 is provided which is configured in particular as a self-aligning bearing, such as a self-aligning rolling bearing or self-aligning sliding bearing, or as a ball joint. The bearing body 220 is inserted into the bearing receptacle 20 along the bore axis 70 and, by means of spring rings 225 inserted into the corresponding grooves 25 inside the bearing receptacle 20, is secured against displacement out of the bearing body 20 in the axial direction of the axis 70. After mounting of the bearing body 220 and arrangement of the strain gauge 30 and of the evaluation and/or control device 35, the linear force measurement device 1 is encapsulated via two housing halves 150 in the region of the webs 40, in order to protect the strain gauges 30 and the evaluation and/or control device 35 from external loads and environmental influences. The evaluation and/or control device 35 and the strain gauge 30 can also be encapsulated by a plastic. The housing halves 150 can then be arranged subsequently around the region of the linear force measurement device 1 between the bearing receptacle 20 and the base 10. The housing halves 150 are dimensioned such that they do not protrude radially beyond the base 10. In particular, a contact edge is provided by the base 10 for application of a union nut 120, with which the linear force measurement device 1 can be fastened to a hydraulic actuator. Such an embodiment is shown in FIG. 3.

Figure 3:
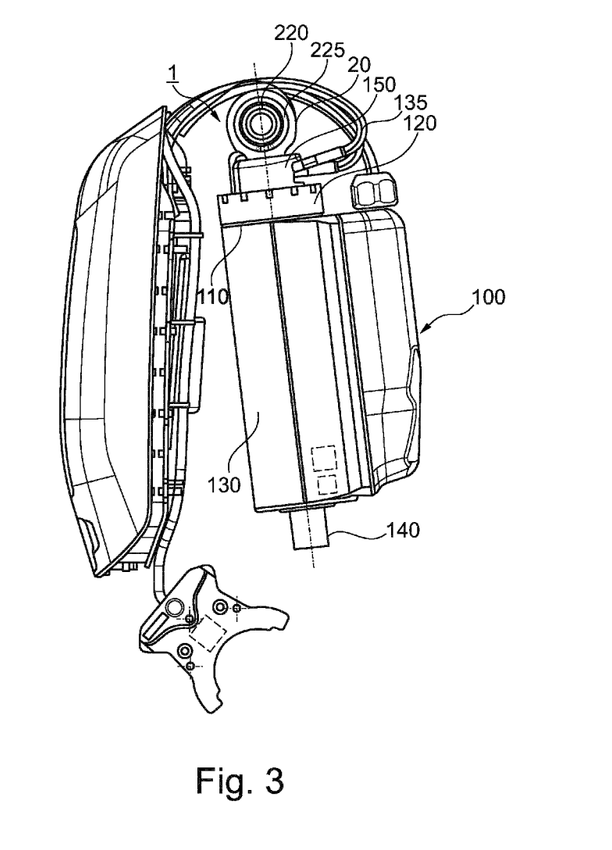
FIG. 3 shows a hydraulic actuator with a mounted linear force measurement device.

FIG. 3 shows a side view of a hydraulic actuator 100 in the form of a hydraulic damper device. The hydraulic actuator 100 has a housing 130 on which is formed a receptacle 110 into which the base 10 is inserted. On its outer face, the receptacle 110 has an external thread which corresponds to an internal thread of the union nut 120. By way of the union nut 120, the base 10 is secured to the housing 130. By way of the cable 135, the measured values of the strain gauge 30 (not shown) are guided out of the housing halves 150 and transmitted to a further control unit via which valves are then controlled, for example, and resistances in the direction of flexion or direction of extension are adjusted. Drives can likewise be activated and deactivated, or energy reservoirs cab be charged and uncharged, in order to bring about an active displacement of the bearing receptacle 20 with the bearing body 120 relative to a second fastening device on the hydraulic actuator 100.

In the illustrative embodiment shown, the linear force measurement device 1 is arranged on a housing 130 of the hydraulic actuator 100. In principle, it is also possible that such a linear force measurement device 1 is arranged on a piston rod of a hydraulic actuator.

Figure 4:
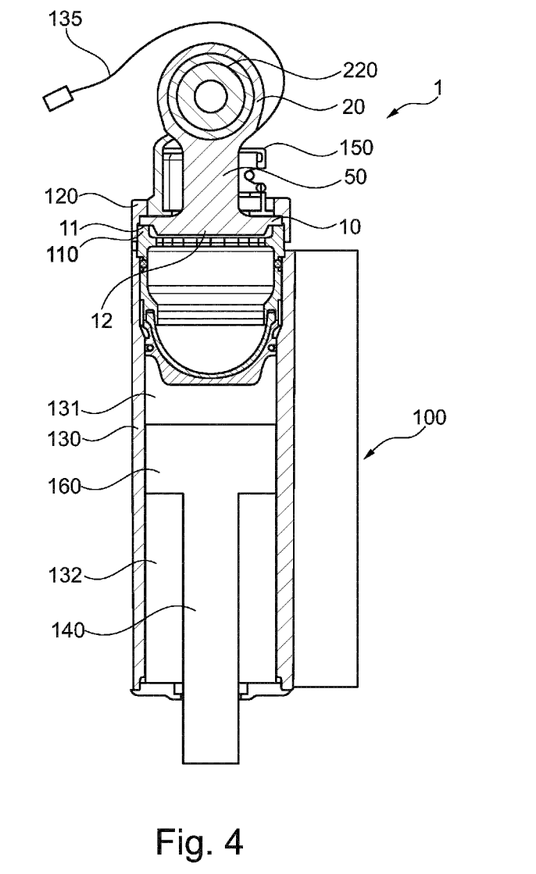
FIG. 4 shows a sectional view of a hydraulic actuator according to FIG. 3.

FIG. 4 shows a sectional view of the hydraulic actuator 100 according to FIG. 3. Inside the housing 130, a hydraulic piston 160 is arranged longitudinally movably on a piston rod 140 and separates a flexion chamber 131 from an extension chamber 132. The receptacle 110 on the housing 130 is of annular shape, such that the base 10 lies with the annular edge 11 on the receptacle 110. By means of the material reduction at the circumference of the base 10, by which the annular edge 11 is formed, a shoulder 12 forms which protrudes in the direction of the housing 10 and thus provides self-centering of the base 10 in the receptacle 110. In the mounted state of the hydraulic actuator 100, the end of the piston rod 140 directed away from the piston 160 is provided with a further fastening device, for example in order to be secured to an upper part or a lower part of a prosthetic joint. A linear force measurement device 1 can likewise be fastened on the piston rod 140 protruding from the housing 130. It is also possible for the linear force measurement device 1 to be fastened exclusively on the piston rod 140, while the housing 130 of the linear actuator 100 without linear force measurement device is fastened to an orthopedic device, for example an orthosis, prosthesis or wheelchair.

Figure 5:
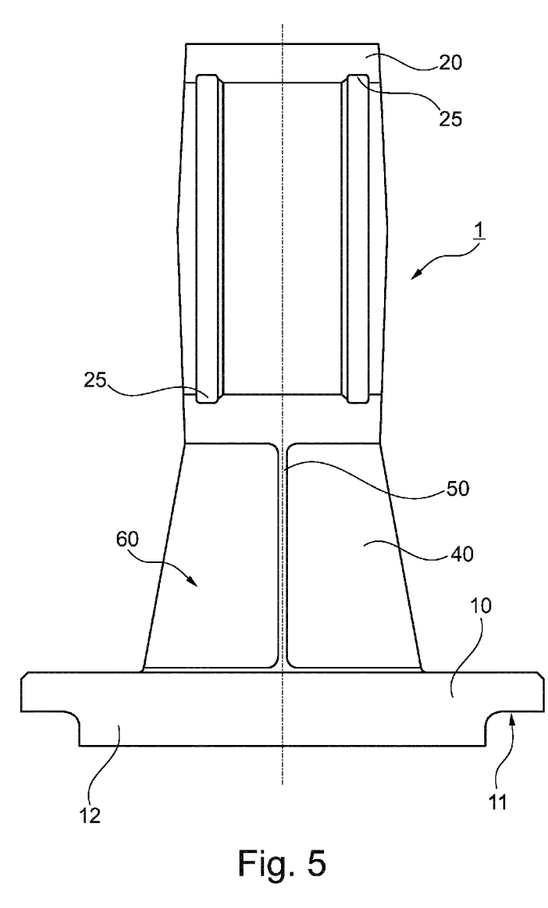
FIG. 5 shows a vertical sectional view of a linear force measurement device.

FIG. 5 shows the linear force measurement device according to FIG. 1 in a vertical section. It will be seen from the sectional view that the base 10 extends substantially horizontally, while the stiffening element 50 in the form of a wall extends perpendicularly thereto in the vertical direction. Spaced apart from its right and left faces, the bearing receptacle 20 has two grooves 25, which are formed circumferentially and serve to receive securing rings (not shown). Extending from the sleeve-shaped bearing receptacle 20 in the direction of the base 10, alongside the integrally formed wall as stiffening element 50, there are two webs 40, of which only one web 40 can be seen in the sectional view. It will be seen in FIG. 5 that the web 40, hence also the second web 40 lying opposite the latter and not shown in the sectional view, has a trapezoidal shape, that is to say that the web 40 is narrower in the region of the bearing receptacle 20 than in the region of the base 10. By virtue of the trapezoidal shape of the webs 40, it is possible to achieve increased stability of the linear force measurement device 1 against deformation of the webs 40. The trapezoidal shape of the webs 40 allows a homogenous strain field to be generated in the region of the sensors 30 or strain gauges. In this way, there is less stress concentration between the webs 40 and the base 10.

In the base 10, an annular edge 11 is formed in the lower region, such that a shoulder 12 forms which points downward away from the bearing receptacle 20. By way of this shoulder 12, which is of circular shape, centering can be achieved in a correspondingly shaped receptacle 110 on the housing of the hydraulic actuator. The main centering is effected via the union nut 120. The shoulder 12 is preferably free and unclamped, in order not to influence the sensor signal. An additional centering effect can be provided by a resilient element between the shoulder 12 and the receptacle 110. The stiffening element 50 is oriented along the direction of action of tensile forces and compressive forces between the bearing receptacle 20 and the base 10. Together with the bearing receptacle 20 and the base 10 and also the webs 40, the stiffening element 50 forms a receiving space 60 in which, for example, control electronics can be accommodated.

Figure 6:
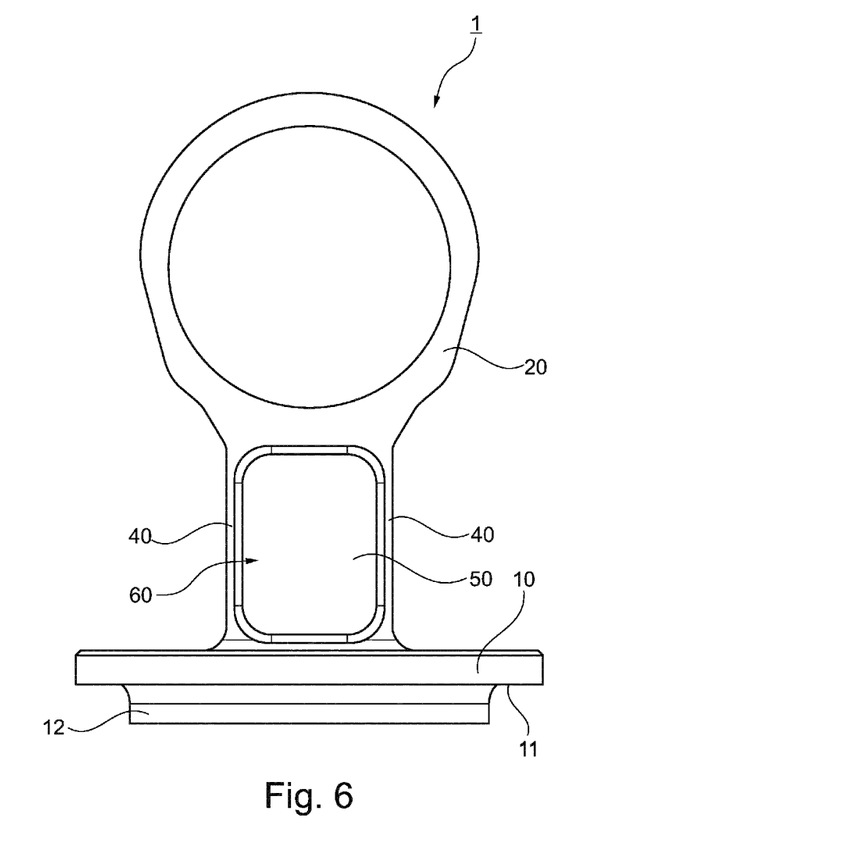
FIG. 6 shows a side view of a linear force measurement device.

FIG. 6 shows the linear force measurement device 1 in a side view. The parallel orientation of the two webs 40 and their perpendicular arrangement with respect to the base 10 can be seen in this perspective. The stiffening element 50 is formed across the whole surface area between the webs 40, the bearing receptacle 20 and the base 10, formed in one piece in the illustrative embodiment shown, the receiving space 60 having an approximately rectangular shape.

Figure 7:
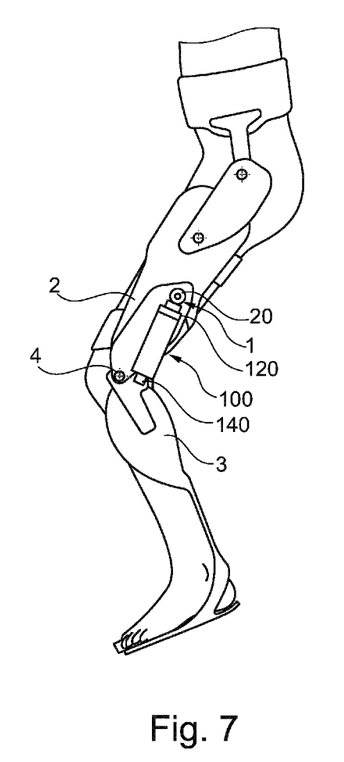
FIG. 7 shows an example of use on an orthosis.

FIG. 7 shows the connection of a hydraulic actuator 100 to an orthosis. In the illustrative embodiment shown, the orthosis bridges all the joints of the lower extremity. The bearing receptacle 20, with the bearing body arranged therein, is fastened to a thigh part 2, which is secured to the thigh by fastening straps. At the proximal end, the thigh part 2 is connected in an articulated manner to a hip strap or a hip shell, and, at the distal end, it is connected in an articulated manner to a lower-leg part 3 via a pivot axis 4, the lower-leg part 3 having a foot support. The lower part 3 is able to pivot about the pivot axis 4 in the direction of extension and the direction of flexion relative to the thigh part 2. The hydraulic actuator 100 is mounted both on the thigh part 2 and also on the lower-leg part 3. The piston rod 140 is fastened to the lower-leg part 3. Pivoting movements between the thigh part 2 and the lower-leg part 3 are assisted or damped by the hydraulic actuator 100. The forces that thereby arise are taken up via the linear force measurement device 1 and transmitted to a control device (not shown), in order either to activate or deactivate drives or to change damping settings.

Figure 8:
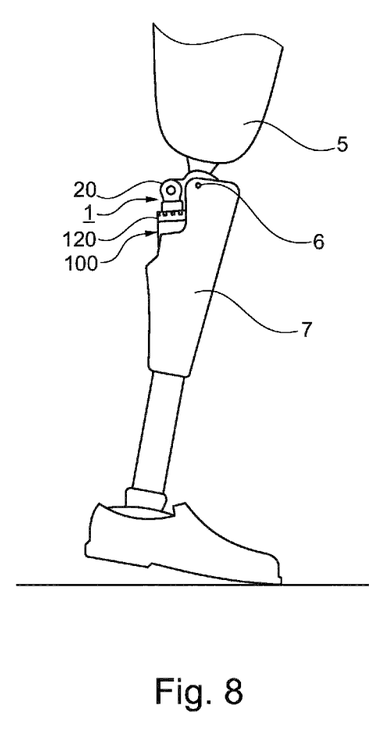
FIG. 8 shows a use of a hydraulic actuator, with a linear force measurement device, in a prosthesis.

An alternative example of use is shown in FIG. 8, in which the hydraulic actuator 100 is arranged between a prosthesis upper part 5, in the form of a thigh socket, and a lower-leg part 7. The upper part 5 and the lower part 7 are connected to each other at a prosthetic knee joint so as to be pivotable about a pivot axis 6. The bearing receptacle 20 of the linear force measurement device 1 is fastened to a bracket on the upper part 5, while the piston rod 140 (not shown) is mounted on the lower-leg part 7. In the event of flexion and extension, the hydraulic actuator 100 is subjected to linear forces, which are measured via the linear force measurement device. Control of the hydraulic actuator 100 can take place on the basis of these measurement results.

We claim:

1. A linear force measurement device for a hydraulic actuator of an orthopedic device, comprising:
    a base;
    a bearing receptacle;
    at least one sensor for detecting changes in length between the base and the bearing receptacle;
    two mutually opposite webs connecting the bearing receptacle to the base;
    a stiffening element arranged between the webs;
    wherein the at least one sensor is fastened to one of the webs, and wherein the base, the bearing receptacle, the webs, and the stiffening element form a receiving space open at only one side.

2. The linear force measurement device as claimed in claim 1, wherein the webs are walls.

3. The linear force measurement device as claimed in claim 1, wherein the webs have a trapezoidal shape and taper in a direction of the bearing receptacle.

4. The linear force measurement device as claimed in claim 1, wherein the webs have a uniform wall thickness.

5. The linear force measurement device as claimed in claim 1, wherein the webs extend in a force action direction of a linear force from the base to the bearing receptacle.

6. The linear force measurement device as claimed in claim 1, wherein the base is a round disk.

7. The linear force measurement device as claimed in claim 1, wherein the bearing receptacle is sleeve-shaped with a round recess.

8. The linear force measurement device as claimed in claim 1, wherein the base, the webs and the bearing receptacle are formed in one piece.

9. The linear force measurement device as claimed in claim 1, wherein the stiffening element is a wall arranged centrally between the webs in a plane of symmetry.

10. The linear force measurement device as claimed in claim 1, wherein the stiffening element is connected to the base, the bearing receptacle, and the webs.

11. The linear force measurement device as claimed in claim 1, wherein the sensor is connected to at least one of an electronic evaluation and a control device, which is arranged in the receiving space.

12. The linear force measurement device as claimed in claim 1, wherein the sensor is secured to the outside of the web.

13. The linear force measurement device as claimed in claim 1, wherein the stiffening element comprises a wall extending an entire width between the webs.

14. The linear force measurement device as claimed in claim 13, wherein the stiffening element is connected to the two webs and the stiffening element is perpendicular to the two webs.

15. A hydraulic actuator for an orthopedic device, having a piston-cylinder unit and a receptacle at or in which a linear force measurement device as claimed in claim 1, is arranged.

16. The hydraulic actuator as claimed in claim 15, wherein the base bears, with its complete surface area or its complete circumference, on the receptacle.

17. The hydraulic actuator as claimed in claim 15, wherein the base is mounted rotatably on or in the receptacle and is fixed by clamping.

18. The hydraulic actuator as claimed in claim 17, wherein the base is fastened to the receptacle via a union nut.

19. The hydraulic actuator as claimed in claim 18, wherein a self-aligning bearing or a ball joint is arranged in the receptacle.

20. The hydraulic actuator as claimed in claim 15, wherein the receptacle is formed or arranged on a housing.

21. A linear force measurement device for a hydraulic actuator of an orthopedic device, comprising:
- a base;
- a bearing receptacle;
- at least one sensor for detecting changes in length between the base and the bearing receptacle;
- two mutually opposite webs connecting the bearing receptacle to the base;
- a stiffening element arranged between the webs and the webs are positioned on opposite sides of the stiffening element;
- wherein the at least one sensor is fastened to one of the webs, and wherein the base, the bearing receptacle, the webs, and the stiffening element form a receiving space open at only one side.

22. A linear force measurement device for a hydraulic actuator of an orthopedic device, comprising:
- a base;
- a bearing receptacle;
- at least one sensor for detecting changes in length between the base and the bearing receptacle;
- two mutually opposite webs connecting the bearing receptacle to the base;
- a stiffening element arranged between the webs and the webs are positioned on opposite sides of the stiffening element;
- wherein the at least one sensor is fastened to one of the webs, and wherein the base, the bearing receptacle, the webs, and the stiffening element form two receiving spaces each open at only one side, and wherein the two receiving spaces are arranged on opposite sides of the stiffening element.

\* \* \* \* \*